US009604006B2

(12) United States Patent
Teucher et al.

(10) Patent No.: US 9,604,006 B2
(45) Date of Patent: Mar. 28, 2017

(54) CARTRIDGE WITH ADJUSTABLE FILLING VOLUME

(75) Inventors: Axel Teucher, Frankfurt am Main (DE); Michael Jugl, Frankfurt am Main (DE)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 18 days.

(21) Appl. No.: 14/233,392

(22) PCT Filed: Aug. 22, 2012

(86) PCT No.: PCT/EP2012/066300
§ 371 (c)(1),
(2), (4) Date: Jan. 17, 2014

(87) PCT Pub. No.: WO2013/026859
PCT Pub. Date: Feb. 28, 2013

(65) Prior Publication Data
US 2014/0148764 A1 May 29, 2014

(30) Foreign Application Priority Data

Aug. 23, 2011 (EP) .................................... 11178401

(51) Int. Cl.
*A61M 5/00* (2006.01)
*A61M 5/315* (2006.01)
*A61M 5/31* (2006.01)

(52) U.S. Cl.
CPC ...... *A61M 5/31511* (2013.01); *A61M 5/3129* (2013.01); *A61M 5/3156* (2013.01); *A61M 5/31533* (2013.01)

(58) Field of Classification Search
CPC ............ A61M 5/3129; A61M 5/31511; A61M 5/31533; A61M 5/3156; A61M 5/00; A61M 2005/005; A61M 5/178; A61M 5/28; A61M 5/283; A61M 5/286; A61M 5/30; A61M 5/315; A61M 2005/31516; A61M 2005/31518
USPC ......................................................... 604/232
See application file for complete search history.

(56) References Cited

U.S. PATENT DOCUMENTS

| 4,636,198 A | 1/1987 | Stade |
| 5,662,612 A | 9/1997 | Niehoff |
| 2013/0296778 A1* | 11/2013 | Damgaard-Soerensen ........... A61M 5/2448 604/82 |

FOREIGN PATENT DOCUMENTS

| CH | 682722 | 11/1993 |
| WO | 2009/137486 A1 | 11/2009 |

OTHER PUBLICATIONS

International Search Report for Int. App. No. PCT/EP2012/066300, completed Nov. 20, 2012.
International Preliminary Report on Patentability for Int. App. No. PCT/EP2012/066300, mailed Dec. 17, 2013.

* cited by examiner

*Primary Examiner* — Jason Flick
(74) *Attorney, Agent, or Firm* — McDonnell Boehnen Hulbert & Berghoff LLP

(57) ABSTRACT

The present invention relates to a cartridge for a drug delivery device, comprising a barrel of substantially cylindrical shape and at least one piston arrangement displaceably arranged in the barrel, wherein the piston arrangement occupies at least 20% of the volume confined by the barrel.

8 Claims, 4 Drawing Sheets

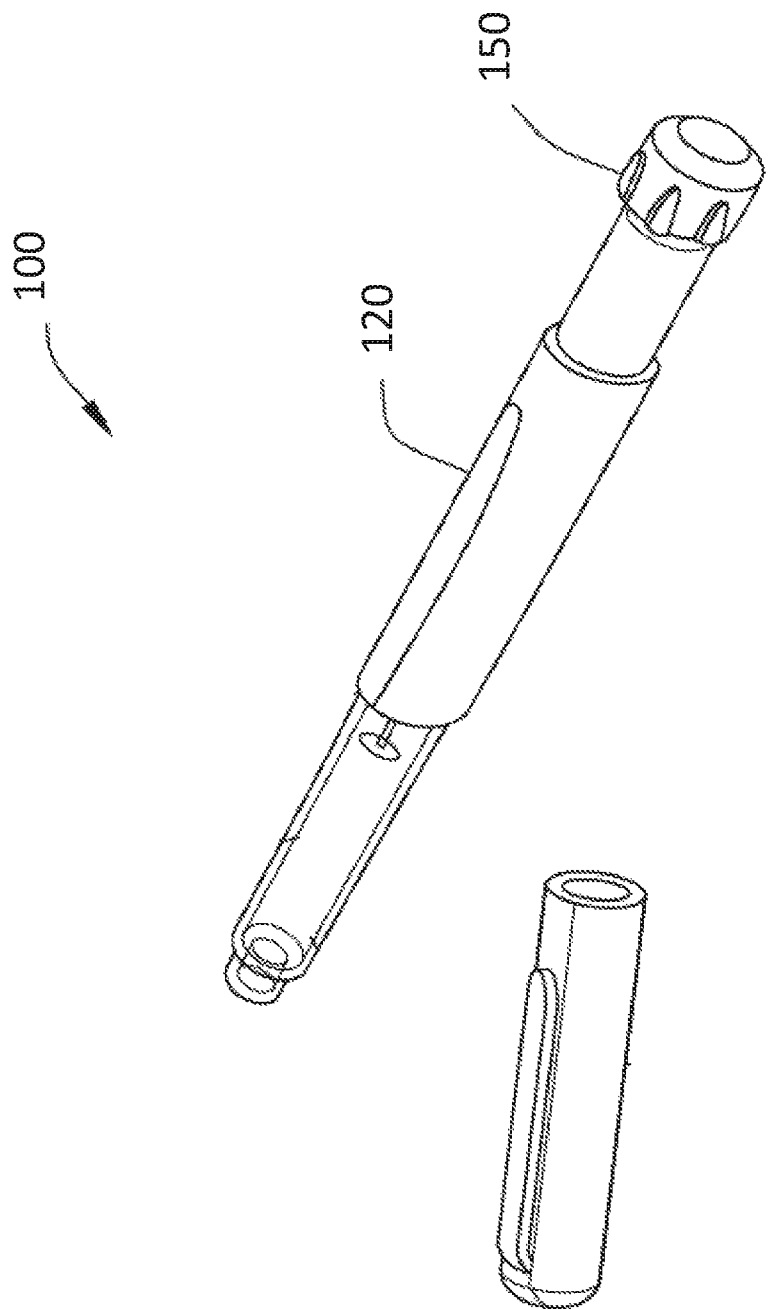

CARTRIDGE WITH ADJUSTABLE FILLING VOLUME

CROSS REFERENCE TO RELATED APPLICATIONS

The present application is a U.S. National Phase Application pursuant to 35 U.S.C. §371 of International Application No. PCT/EP2012/066300 filed Aug. 22, 2012, which claims priority to European Patent Application No. 11178401.3 filed Aug. 23, 2011. The entire disclosure contents of these applications are herewith incorporated by reference into the present application.

TECHNICAL FIELD

The present invention relates to the field of storage and transportation as well as administering of liquid medicaments. In particular, the invention relates to cartridges or comparable storage or dispensing containers designed and adapted for storing, transporting as well as for dispensing of a pre-defined dose or amount of the medicament provided therein.

BACKGROUND

Liquid medicaments or drugs have to be stored and transported by way of sealed containers, such like carpules, ampoules, vials or infusion bottles. Most of the known containers comprise a vitreous body made of a material being substantially inert to the medicament stored therein. Such storage units for liquid medicaments may also provide controlled and well-defined dispensing of the medicament provided therein. In particular with carpules or cartridges, a tubular or cylindrical vitreous barrel is sealed at one end by way of a piston slidably disposed in the barrel.

When applying thrust or pressure to the piston, e.g. in a distal direction, a pre-defined dose of the medicament can be expelled from the interior volume of such a container, provided that its opposite, hence distal outlet is coupled with or is in fluid-connection with e.g. a piercing assembly, like an injection needle.

There generally exists a large variety of different cartridges 10, 20, 30 as for instance depicted in FIGS. 1*a*, 1*b* and 1*c*. Depending on the type of the medicament stored therein and the particular application or administering scheme, the medicament should be administered or dispensed, the cartridges 10, 20, 30 comprise different filling volumes 16, 26, 36 and a rather large variety of peripheral geometries.

A standard cartridge 10 is for instance schematically depicted in FIG. 1*a*. This cartridge 10 comprises a vitreous tubular body 12 defining an inner volume 16 that can be filled with a medicament to be dispensed. At the upper, proximal end section, the cartridge 10 comprises a piston 14 being displaceable in distal direction towards the lower outlet end of the cartridge 10.

In comparison to the cartridge 10 according to FIG. 1*a*, FIG. 1*b* illustrates another cartridge 20 having a barrel 22 being smaller in diameter. However, axial elongation of cartridges 10, 20 and of their respective vitreous barrels 12, 22 is substantially identical. Also the axial size of the pistons 14, 24 is substantially the same. As a consequence, a pressure receiving or proximal end face 18, 28 of the respective pistons 14, 24 of the cartridges 10, 20 as depicted in FIGS. 1*a* and 1*b* is located at the same position relative to the respective barrel 12, 22.

In fact, the available filling volume 26 of cartridge 20 is much smaller than the filling volume 16 of cartridge 10.

In FIG. 1*c*, another common type of a cartridge 30 is illustrated. In comparison with cartridge 10 as depicted in FIG. 1*a*, the cartridge 30 comprises a reduced axial length but its barrel 32 features a diameter being substantially comparable to the diameter of the barrel 12. Even though the geometry and shape of the cartridges 20, 30 drastically differs, their available filling volume 26, 36 may be in the same range. Due to the reduced length, the proximal end face 38 of the piston 34 of the cartridge 30 drastically differs from the positions of the proximal end faces 18, 28 of the cartridges 10, 20 as shown in FIGS. 1*a* and 1*b*.

Since drug delivery devices, such like pen-type injectors making use of such cartridges 10, 20, 30 are produced in a mass production environment, the large variety of cartridge volumes and cartridge geometries provides an undue burden for the manufacturing of the device and/or for a filling process of such cartridges. Hence, for different filling volumes of various cartridges 10, 20, 30 different types of barrels 12, 22, 32 and pistons of variable size 14, 24, 34 have to be ordered, stored and supplied to the respective assembly or filling line.

Moreover, when cartridges of different size are to be filled with a medicament, a respective filling or assembly line for the cartridges must be reconfigured. The geometric variance and the large spectrum of cartridge sizes and shapes therefore comes along with various drawbacks for a mass production process. Moreover, repeated reconfiguration of a mass production process is always accompanied with rising costs and with a decreased occupancy of generally available production or filling lines.

It is therefore an object of the present invention to provide a cartridge design by way of which the above mentioned drawbacks can be substantially set aside. The invention focuses on a smooth and easy as well as on a cost-efficient solution to provide a variety of cartridges having different filling volumes. The invention particularly focuses on a cost-efficient implementation in a mass production process and intends to reduce tooling times for automated assembly- and filling lines as well as to reduce costs for manufacture and transport of cartridges.

SUMMARY

The present invention relates to a cartridge for a drug delivery device. The cartridge comprises a barrel, preferably a vitreous barrel, having a substantially cylindrical shape. The cartridge further has at least one piston arrangement displaceably arranged in the barrel. The piston arrangement occupies at least 20% of the volume confined by the barrel. By having a piston or piston arrangement occupying a comparatively large volume or percentage of the barrel, a residual volume of the barrel to receive and to be filled with a pre-defined amount of a medicament can be accordingly adjusted.

It is therefore intended to increase the size, in particular the axial extension of the piston arrangement at the expense of the available and remaining filling volume of the barrel. This way, even an entire set of cartridges, with cartridges having different filling volumes can be provided, wherein the outer contour and geometry of the various cartridges can remain substantially unmodified.

This way, the external geometry and shape of a cartridge can be standardized and different filing volumes to be provided by different cartridges can be adjusted only by increasing or decreasing the size of the piston arrangement of said cartridges.

According to a preferred aspect, the piston arrangement of the cartridge occupies at least 30%, 35%, 40%, 45%, 50%, 55%, 60%, 65%, 70%, 75% or even 80% of the volume confined and generally provided by the barrel geometry. This way, by appropriately selecting and adjusting a piston arrangement of a cartridge, the available filling volume of the cartridge can be modified from 20% to 80% of the volume being confined by the substantially cylindrical barrel. Generally, the size of the piston arrangement is not strictly restricted to the above-mentioned percentage numbers but may be varied continuously in order to match with given requirements.

According to a further aspect, the piston arrangement to be arranged in the barrel comprises a set of pistons, wherein each piston has a substantially identical diameter in the transverse plane but comprises different axial elongation. Modification of the size or volume of the piston arrangement therefore corresponds to a modification or selection of the axial elongation of the respective piston.

This can either be attained by providing numerous pistons, each of which being different with respect to their axial extension. Alternatively and according to another preferred aspect, the piston arrangement comprises at least two individual pistons adjacently arranged in axial direction. Based on a standard sized piston, a piston arrangement of variably length can be attained having a geometrical size being an integral multiple of said standard volume.

In particular, when the piston arrangement comprises at least two or even more pistons, it is of further benefit, when the pistons mutually abut with a distal and/or proximal end face. Hence, the plurality of pistons of a piston arrangement disposed in the barrel of the cartridge should be in direct contact with each other in order to minimize geometric tolerances of the various components and their assembly.

According to a further preferred aspect, the axial elongation of the piston arrangement is selected in order to provide a pre-defined residual filling volume of the barrel. The residual filling volume generally calculates as the overall inner volume of the barrel subtracted by the volume of the piston arrangement to be arranged therein by further taking into account the axial position of the piston relative to the barrel.

In this context it is further to be noted, that axial elongation or axial direction corresponds to the long axis of the tubular shaped barrel, which substantially coincides with the axis of symmetry of the barrel or cartridge.

Furthermore, the cartridge, hence the volume confined by the barrel and/or by the piston may be at least partially filled with a medicament.

According to a further independent aspect, the invention also relates to a set of cartridges comprising at least two cartridges, each of which having a barrel of substantially cylindrical shape and at least one piston arrangement displaceably arranged therein. Any one of said at least two cartridges comprises a substantially identical peripheral geometry and/or shape and comprises a piston arrangement of different axial elongation in order to individually modify the available filling volume of each cartridge. This way, a large variety of cartridges can be provided, each of which featuring a substantially identical or standardized peripheral geometry but provide different filling volumes that match with given medication requirements.

In a further embodiment, the proximal end face of the piston arrangement of the at least two cartridges of the set of the cartridges is located at the same position relative to respective barrels of said cartridges. By arranging the thrust receiving or proximal end face of a piston arrangement always at a well-defined position relative to the barrel, different cartridges of the set of cartridges can be arbitrarily replaced in a particular drug delivery device. Hence, individual cartridges of a set of cartridges are designed as being substantially compatible and/or interoperable.

In a further independent aspect, the invention also relates to a drug delivery device for setting and dispensing of a pre-defined dose of a liquid medicament. The device comprises a housing to accommodate a cartridge as described above. The device further comprises a drive mechanism having at least a piston rod to operably engage with the piston arrangement of the cartridge in order to exert a distally directed pressure to the piston arrangement. The drive mechanism may also provide a dose setting operability, such that a user may individually specify a size of a dose to be injected by the drug delivery device.

Typically, the drug delivery device is designed as a pen-type injector, wherein the cartridge is either replaceably or non-replaceably mounted in the housing. With a non-replaceable cartridge, the entire device is designed as a disposable device and is intended to be discarded as a whole when the content of the cartridge is used up.

The invention also reflects in a method to modify the filling volume of a cartridge, wherein the cartridge has a barrel of pre-defined size and/or geometry. The method comprises the steps of selecting at least one of a plurality of pistons of variable axial length or axial elongation. After selection of a suitable piston, the at least one selected piston is arranged in the barrel of the cartridge in order to adjust the residual filling volume of the cartridge to a pre-defined size, which is then to be filled with the medicament to be stored and/or to be provided in the cartridge.

In order to match the required size of the filling volume, also a plurality of pistons that are substantially equal or different in size can be positioned in the barrel, preferably in a densely packed or stacked configuration. This way, a distally directed displacement of a proximally located piston can be transferred and directly propagated to a distally located piston which confines the available residual filling volume of the cartridge in proximal direction.

With the described adjustment of the filling volume of a cartridge, the number of barrels of different geometry and shapes can be remarkably reduced. Also, tooling time of filling or assembly lines in a mass production process can be beneficially reduced. In effect, costs for production, manufacture, logistics and storage can be substantially minimized.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro37, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described by making reference to the drawings in which:

FIG. 4 illustrates an example of a drug delivery device 100 in the form of a pen type syringe. This drug delivery device 100 comprises a housing 120, which contains a drive mechanism 150.

DETAILED DESCRIPTION

Figures 1A, 1B, 1C:
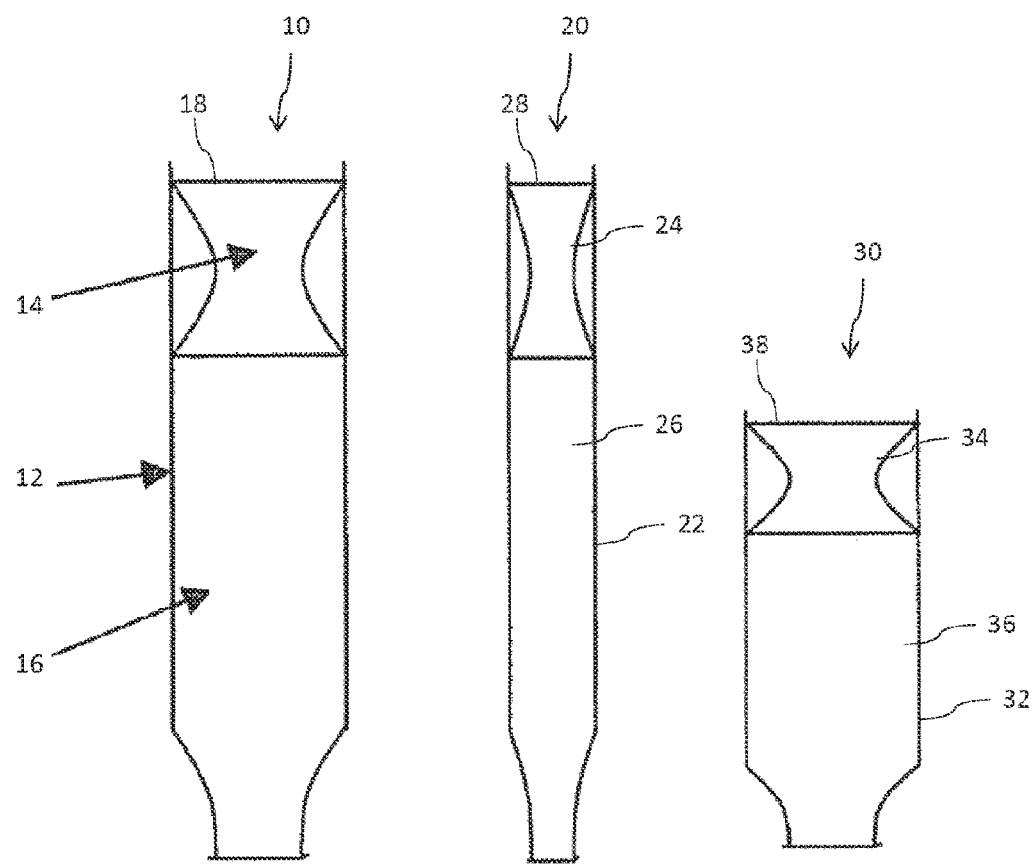
FIG. 1*a* shows a standard cartridge according to the prior art.
FIG. 1*b* is illustrative of a standard cartridge as known in the prior art with a reduced filling volume and FIG. 1*c* shows another cartridge geometry with a reduced filling volume.
Figure 2A:
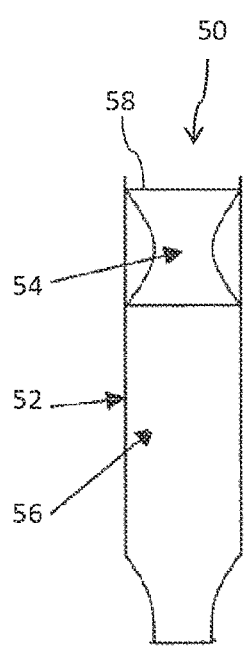
FIG. 2*a* is illustrative of a cartridge according to the present invention.
Figure 2B:
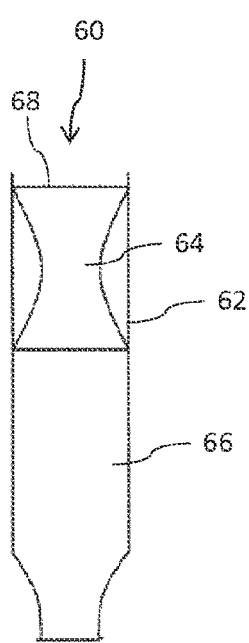
FIG. 2*b* shows a filling volume-modified cartridge.
Figure 2C:
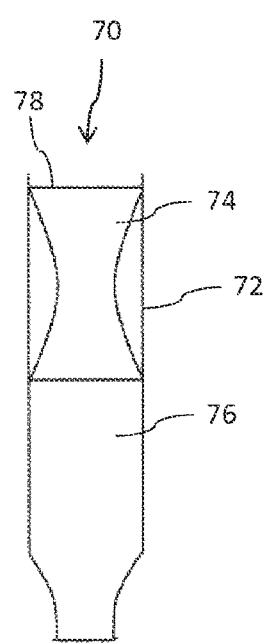
FIG. 2*c* shows another volume-reduced cartridge with a piston of increased size.

The cartridges 50, 60, 70 as illustrated in FIGS. 2*a*, 2*b*, and 2*c* belong to a set of cartridges, wherein individual cartridges 50, 60, 70 comprise a barrel 52, 62, 72 of substantially identical shape and geometry. In order to reduce or to adjust a filling volume 56, 66, 76 to be filled with a liquid medicament, the axial, hence vertical size of the individual pistons 54, 64, 74 of the cartridges 50, 60, 70 varies.

For instance, the size of the piston 64 of the cartridge 60 is increased compared to the size of the piston 54 in such a way, that the residual available filling volume 66 of the cartridge 60 is reduced to a factor of e.g. ⅔ compared to the available filling volume 56 of cartridge 50.

Similarly, the axial extension of the piston 74 of the cartridge 70 according to FIG. 2c is even larger than the extension of the piston 64 of the cartridge 60 according to FIG. 2b. Consequently, the residual filling volume 72 of said cartridge 70 may be reduced to ½ compared to the filling volume 56 of cartridge 50.

Figures 3A, 3B:
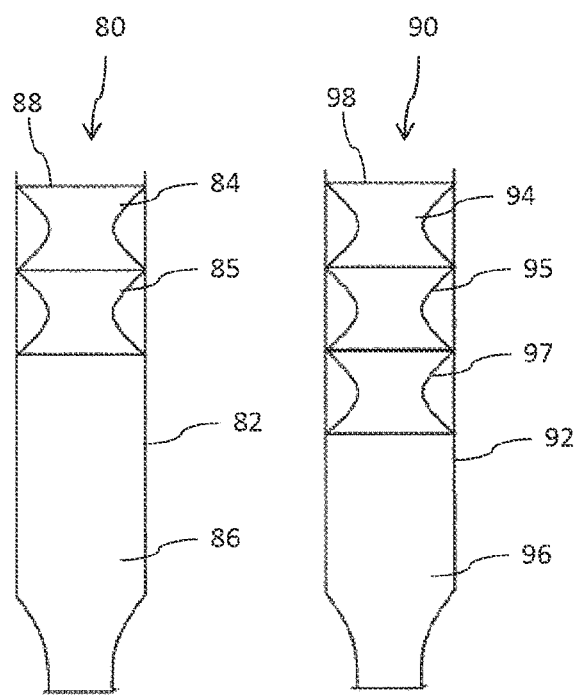
FIG. 3*a* illustrates another cartridge embodiment featuring two adjacently arranged pistons.
FIG. 3*b* shows another embodiment, wherein a piston arrangement comprises three adjacently arranged pistons to reduce the available filling volume of the cartridge.

In a similar way, FIGS. 3a and 3b illustrate two alternative embodiments of cartridges 80, 90, wherein a piston arrangement confining a residual filling volume 86, 96 of the respective barrels 82, 92 of the cartridges 80, 90 comprises two or even three individual pistons 84, 85 or 94, 95, 97, respectively. With the embodiments according to FIG. 3a and FIG. 3b, it is intended, that the individual pistons 84, 85 and 94, 95, 97 mutually abut in axial direction, such that a displacement of a proximal piston 84, 94 in distal direction is substantially unalteredly transferred to a respective displacement of a distally located piston 85, 97 of the respective piston arrangement.

With the embodiments as depicted in FIGS. 2a to 3b it is further to be noted, that proximal end faces 58, 68, 78, 88, 98 of the various piston arrangements 54, 64, 74, 84, 85, 94, 95, 97 are located in the same position relative to the respective barrel 52, 62, 72, 82, 92 of the illustrated cartridges 50, 60, 70, 80, 90. This way, various cartridges 50, 60, 70, 80, 90 of a set of cartridges are substantially compatible with each other and do not require modifications of a drug delivery device to be operably engaged with said cartridges 50, 60, 70, 80, 90 and their pistons 54, 64, 74, 84, 94.

The invention claimed is:

1. A set of cartridges for a drug delivery device comprising at least a first and a second cartridge,
wherein the first and the second cartridges are configured for a replaceable- or non-replaceable mounting in a housing of the drug delivery device, and
wherein the first cartridge and the second cartridge each comprise a barrel of substantially cylindrical shape with a cylinder long axis extending along an axial direction, wherein the shape of a first barrel of the first cartridge is substantially identical to the shape of a second barrel of the second cartridge, and wherein the first cartridge comprises a first piston arrangement having one or more pistons and wherein the second cartridge comprises a second piston arrangement having one or more pistons and wherein a combined total axial length of the one or more pistons of the first piston arrangement is of different axial length than a combined total axial length of the one or more pistons of the second piston arrangement such that an available filling volume of the first cartridge is different from that of the second cartridge when the first and the second piston arrangements each have a proximal end face located at the same position relative to the respective first barrel and the second barrel, the first and second piston arrangements are displaceably arranged in the first and second barrels, respectively, wherein the first and second piston arrangements each occupy at least 20% of a volume confined by the respective first barrel and second barrel.

2. The set of cartridges according to claim 1, wherein the first piston arrangement occupies at least 30%, 35%, 40%, 45%, 50%, 55%, 60%, 65%, 70%, 75% or even 80% of the volume confined by the first barrel, wherein the second piston arrangement occupies at least 30%, 35%, 40%, 45%, 50%, 55%, 60%, 65%, 70%, 75% or even 80% of the volume confined by the second barrel.

3. The set of cartridges according to claim 1, wherein at least one of the first or the second piston arrangements comprises at least two individual pistons, and wherein the at least two pistons mutually abut each other with a distal and/or proximal face.

4. The set of cartridges according to claim 1, wherein the axial length of each of the first piston arrangement and the second piston arrangement is selected in order to provide a predefined residual filling volume of each of the first and the second barrels, respectively.

5. The set of cartridges according to claim 1, wherein the cartridges are at least partially filled with a medicament.

6. The set of cartridges according to claim 1, wherein the first barrel and the second barrel are substantially identically shaped.

7. A drug delivery device for setting and dispensing of a predefined dose of a medicament, comprising:
a housing to accommodate a first cartridge from the set of cartridges according to claim 1, and
a drive mechanism having a piston rod to operably engage with the first piston arrangement of the first cartridge.

8. A method to modify the filling volume of a cartridge from the set of cartridges according to claim 1, the first cartridge having a first barrel of predefined size and/or geometry, the method comprising the steps of:
selecting a first piston from a plurality of pistons of variable length, and
arranging the selected first piston in the first barrel of the first cartridge to adjust the residual filling volume of the first cartridge to a predefined size.

* * * * *